United States Patent

Chou

[11] Patent Number: 6,083,218
[45] Date of Patent: *Jul. 4, 2000

[54] METHOD AND APPARATUS FOR REMOVING DENTAL CARIES BY USING LASER RADIATION

[75] Inventor: Mau-Song Chou, Rancho Palos Verdes, Calif.

[73] Assignee: TRW Inc., Redondo Beach, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/676,695

[22] Filed: Jul. 10, 1996

[51] Int. Cl.$^7$ .................................................. A61N 5/06
[52] U.S. Cl. .................................. 606/10; 606/3; 606/15; 606/17; 433/29; 433/215
[58] Field of Search ............................. 606/2–14; 433/29, 433/215

[56] References Cited

U.S. PATENT DOCUMENTS

| | | | |
|---|---|---|---|
| 5,112,328 | 5/1992 | Taboada et al. | 606/5 |
| 5,116,227 | 5/1992 | Levy . | |
| 5,123,902 | 6/1992 | Müller et al. | 606/12 |
| 5,180,304 | 1/1993 | Vassiliadis et al. . | |
| 5,199,870 | 4/1993 | Steiner et al. . | |
| 5,281,141 | 1/1994 | Kowalyk . | |
| 5,324,200 | 6/1994 | Vassiliadis et al. . | |
| 5,342,198 | 8/1994 | Vassiliadis et al. . | |
| 5,435,724 | 7/1995 | Goodman et al. . | |

OTHER PUBLICATIONS

Henning, et al., "Caries selective ablation by pulsed lasers," SPIE 1424, pp. 99–105 (1991).

Arima, et al., Effects of ArF excimer laser irradiation on human enamel and dentine, Lasers in Surgery and Medicine 13 97 to 105 (1993).

Frentzen, et al., "Excimer lasers in dentistry: future possibilities and advanced technology," Quintessence International 23, 117 to 133 (1992).

Neev, et al., "Selectivity, efficiency, and surface characteristics of hard dental tissues ablated with ArF pulsed excimer lases," Lasers in Surgery and Medicine 11, 499 to 510 (1991).

Selective Absorption of Ultraviolet Laser Energy by Human Atherosclerotic Plaque Treated with Tetracyclines by Murphy–Chutorian et al; Am. J. Cardiol; vol. 55; May 1985; pp 1293–1297.

*Primary Examiner*—David M. Shay
*Attorney, Agent, or Firm*—Michael S. Yatsko

[57] ABSTRACT

An apparatus (1) is provided for treating a target area (22) of a tooth (10). The apparatus (1) generally comprises a coolant delivery system (20) and an ultraviolet laser system (15). The coolant delivery system (20) delivers coolant (52) to the target area (22) while a light guide (44) focuses ultraviolet radiation thereon. The ultraviolet radiation (18) and coolant (52) combine to ablate a desired material without generating excess heat which may otherwise char surface tissue or cause thermal damage.

18 Claims, 2 Drawing Sheets

METHOD AND APPARATUS FOR REMOVING DENTAL CARIES BY USING LASER RADIATION

BACKGROUND OF THE INVENTION

1. Technical Field

The present invention generally relates to an apparatus and method for removing plaque and decay tissue, commonly known as dental caries, using laser radiation. More particularly, the present invention relates to an apparatus using ultraviolet radiation and a coolant to ablate a desired material from a tooth without generating excess heat at the target site or surrounding areas.

2. Discussion

As is generally known in the art of dentistry, conventional drilling machines for treating dental caries such as plaque and decay tissue can be inaccurate and painful. Therefore, it is desirable to replace or support conventional drilling machines with lasers in order to achieve a more accurate and painless treatment of caries. However, laser irradiation processes currently available often produce charring on the target surface and surrounding areas due to laser generated heat. The blackened char tissue effectively blocks the laser radiation thereby preventing it from reaching biological tissue thereunder. Thus, charring due to excess heat interrupts the ablation process.

Excess heat may also produce cracks in the tooth surface and damage the nerve system and other pulp structure in the pulp chamber irreversibly. Accordingly, laser treatment of hard tissue, including caries removal, has not yet achieved practical dental application due to the thermal damage related to laser generated heat. Therefore, it is desirable to provide an apparatus and method for treating dental caries using laser irradiation which does not generate sufficient heat to cause thermal damage.

In conventional dental surgery using drilling machines, water is commonly used to dissipate heat and remove debris from a work area. Water has also been used in laser dental surgery for the removal of excess heat after irradiation of a target area with laser pulses. For example, Vassiliadis, et al. (U.S. Pat. No. 4,940,411) discloses a dental laser method using a Neodymium doped Yttrium-Aluminum-Garnet (Nd:YAG) infrared laser.

Vassiliadis, et al. teach spraying water on a tooth following each laser pulse. Thereafter, the tooth is dried prior to a subsequent pulse from the laser. This teaching conforms with studies concerning infrared laser treatment of dental caries which stress the need to keep the tooth dry during delivery of laser pulses in order to minimize attenuation of the laser by the water. During infrared laser treatment, water has to be nearly absent due to the laser being strongly absorbed. A drying means, such as an air sprayer is generally used to dry the tooth surface before a subsequent laser pulse is applied.

On the other hand, Wolbarsht, et al. (U.S. Pat. No. 5,267,856) discloses that a thin layer of water entering the surface pores or chemically held on the surface of the tooth can enhance the removal rate of desired material when using an Erbium doped Yttrium-Aluminum-Garnet (Er:YAG) infrared laser. Wolbarsht stresses that the water should not be permitted to remain pooled on the tooth surface in this process because of the inability of the infrared radiation to penetrate thick layers of water effectively. Therefore, the thickness of the water layer must be critically controlled during the process.

One problem with infrared lasers is that they are not selective in treating carious tissue without effecting dentine and enamel. Furthermore, infrared laser light cannot penetrate through water except over relatively short distances. Therefore, infrared processes exclude the use of a relatively thick layer of water spray to achieve effective cooling. Accordingly, it is desirable to provide a laser which is selective in removing carious material and which penetrates thick layers of water. In this way, water can be sprayed on the tooth surface in a non-critically controlled manner such that it may pool or form a thick layer thereon which is effective to prevent charring of tissue. Furthermore, the thick layer of water provides a greater cooling effect and allows use of greater laser fluence which improves the ablation process rate.

SUMMARY OF THE INVENTION

An apparatus is provided for treating a target area of a tooth. The apparatus generally comprises a coolant delivery system and an ultraviolet laser. The coolant delivery system delivers coolant to the target area while a light guide focuses the ultraviolet radiation thereon. The laser and coolant combine to ablate a desired material without generating excess heat which may char surface tissue or cause thermal damage.

DETAILED DESCRIPTION OF THE PREFERRED EMBODIMENTS

The present invention provides an apparatus and method for removing dental caries such as plaque, decay tissue and lesions using ultraviolet laser radiation and a coolant. The use of laser radiation enables a more accurate and painless treatment of caries than conventional drilling machines. The present invention effectively removes dental caries from hard surfaces and prevents charring of tissue at the target area by preventing excess heat from being generated. By preventing charring of tissue at the target area, the ablation process can be executed without interruption. Also, the potential for dentine or enamel cracking as well as damage to the nerve system and other pulp structure in the pulp chamber is greatly reduced by preventing excess heat from being generated at the target and surrounding areas. Furthermore, the thickness of the coolant layer on the tooth surface does not need to be critically controlled. Thus, the coolant used in the present invention may remain pooled on the tooth surface during laser irradiation. Moreover, a drying step, as required in previous processes, is eliminated.

Figure 1:
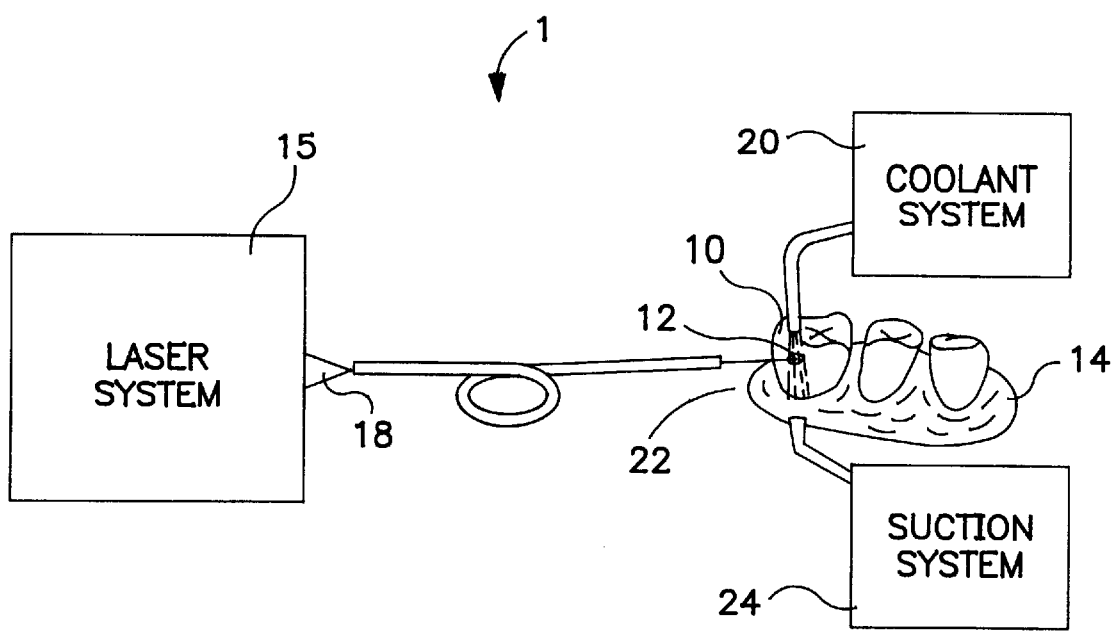
FIG. 1 is a schematic view of an apparatus for removing dental caries such as plaque and decay tissue including an ultraviolet laser and a coolant in accordance with the present invention.

In FIG. 1, an apparatus for removing dental caries, such as plaque and decay tissue, implementing the present invention is shown generally at 1. A tooth 10 having carious material or decay tissue 12 located thereon is shown protruding from a gum 14. A laser system 15 is provided to serve as a source of ultraviolet radiation 18 for the apparatus 1. A coolant delivery system, generally indicated at 20, is provided for delivering coolant to the target area 22. A suction system, indicated at 24, is provided for collecting excess coolant and debris from the target area 22.

Figure 2:
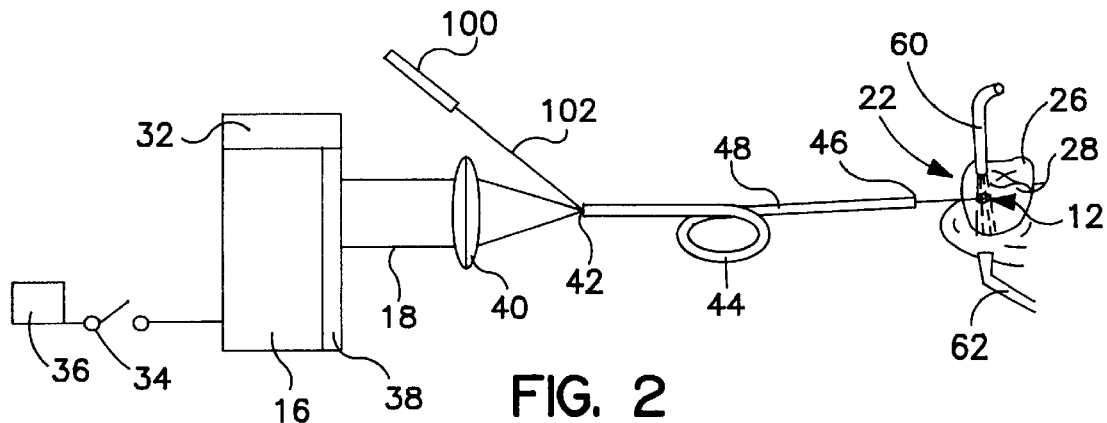
FIG. 2 is a more detailed schematic view of the apparatus of FIG. 1.

Referring now to FIG. 2, the present invention utilizes an ultraviolet laser generator 16 to generate pulsed ultraviolet radiation 18 having a wavelength generally less than 600 nm. The ultraviolet laser generator 16 of the present invention may be set to operate at a predetermined fluence to selectively ablate a single target material since healthy enamel 26, healthy dentin 28, and carious lesions 12 each have different energy fluence thresholds for ablation, as well as different absorption coefficients which describe the characteristic depths to which ultraviolet radiation 18 is absorbed. The use of the ultraviolet laser generator 16 advantageously permits selective ablating of caries 12 while leaving healthy dentin 28 and enamel 26 essentially unaffected.

Furthermore, a conventional control panel 32 provides means for adjusting the frequency, energy, and duration of the pulses of radiation 18 generated by the laser 16. An activation switch 34 is coupled between the laser 16 and a power supply 36 to activate the laser 16.

The laser generator 16 preferably produces a pulsed output beam 30 with a pulse repetition rate of from about 0.1 to about 10,000 pulses per second and laser energy of about 0.1 millejoules per pulse to 5 joules per pulse. In addition, the laser 16 has a wavelength approximately between 193–600 nm which has been shown to be particularly effective in eradicating caries 12. The diameter of the output beam 30 at the target area 22 is preferably between 0.1 mm to 5 mm.

Although not to be interpreted as limiting, the following lasers have been found to be particularly useful in conjunction with the present invention: Argon-Fluoride (ArF) at approximately 193 nm; Krypto-Fluoride (KrF) at approximately 249 nm; Xenon-Chloride (XeCl) at approximately 305 nm; Xenon-Fluoride (XeF) at approximately 352 nm and frequency tripled Neodymium doped Yttrium-Aluminum-Garnet (Nd:YAG) at approximately 355 nm.

Conventional optics 38 such as mirrors, lenses or prisms are optionally employed to direct the radiation 18 from the laser 16 to a lens 40. The lens 40 directs and focuses the radiation 18 into one end 42 of a light guide 44. It should be noted that the lens 40 can include more than one element and can be shaped to any number of configurations and focal lengths as desired. Furthermore, an optical output connector (not shown) can be interposed between the laser 16 and the light guide 44 if desired.

The light guide 44, which may be an optical fiber or a conventional mirror and lens system, is provided to direct and transfer the radiation 18 along its interior to an exit end 46. In the preferred embodiment, an optical fiber is used since its flexibility and ease of positioning facilitates operation within the confines of a human mouth. Preferably, a triple frequency Nd:YAG laser is employed when an optical fiber is used.

The exit end 46 is preferably shaped so as to concentrate or focus the output beam 30 exiting therefrom. Alternately, a lens may be attached to the exit end 46 for this purpose. In either case, it is desirable to provide a relatively short focal length at the exit end 46 for most dental applications. The output beam 30 exiting from the exit end 46 is used to ablate carious material 12. It should be noted that the light guide 44 may be incorporated into a hand piece at its free end 48 so as to provide ease of operation for a dentist.

In the preferred embodiment of the present invention, a low power laser 100 operating in the visible spectrum is incorporated into the laser system 15. Helium Neon or Diode lasers are suitable for this purpose. A guide beam 102 exiting the low power laser 100 travels through the light guide 44 so as to be substantially coincident with the output beam 30 when projected from the exit end 46. In this way, the output beam 30 can be guided to the target area 22 by observing the position of the guide beam 102. In the case when the low power laser 100 is not used, the operator may observe visible fluorescence on the target area 22 induced by the radiation 18 for an indication that the output beam 30 is properly positioned.

Figure 3:
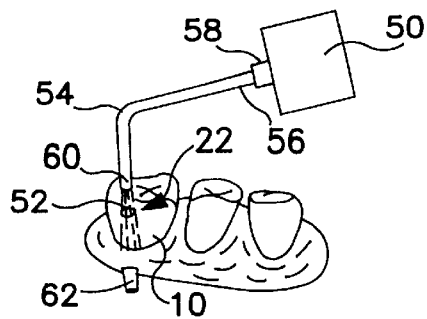
FIG. 3 is a detailed schematic view of the coolant delivery system of FIG. 1.

Turning now to FIG. 3, a coolant reservoir 50 is provided for storing coolant, preferably in the form of water 52 cooled to a temperature in the range of 15° C. to 30° C. to be applied to the tooth 10. A tube or supply line 54 is coupled at a first end 56 through a connection means 58 to the coolant reservoir 50. The tube 54 is positionable for directing water 52 from an exit end 60 to the target area 22. The water 52 may be delivered intermittently or preferably continuously over the tooth 10. Known water delivery systems such as a conventional air/water dental handpiece as found in most dental offices can be used effectively for this purpose.

It should be noted that although the coolant preferably comprises water 52 in the form of a spray, other coolants may be used. It is also preferable that distilled or deionized water 52 be utilized with lower wavelength lasers such as the ArF laser so as to minimize the level of contaminants which may absorb the laser radiation 18. However, the preference for distilled or deionized water 52 decreases as the wavelength of the laser 16 increases.

Figure 4:
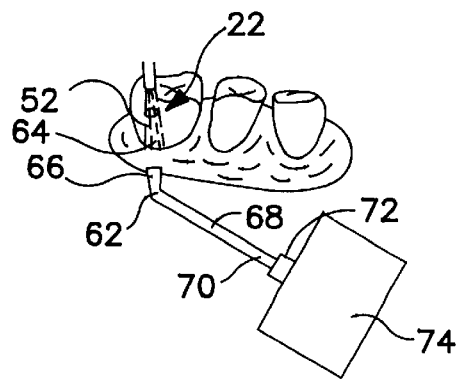
FIG. 4 is a detailed schematic view of the suction system of FIG. 1.

Referring to FIG. 4, a suction tube 62 is provided for removing excess water 52 and debris 64 from the target area 22. The suction tube 62 has a first end 66 adapted for collecting and delivering excess water 52 to an elongated body portion 68. The suction tube 62 also includes an exit end 70 which is coupled by a connection means 72 to a waste system 74. Conventional suction systems as found in most dental offices are preferred for this purpose.

In operation, the low power laser 100 is activated so as to cause the guide beam 102 to exit the light guide 44. Next, the free end 48 of the light guide 44 is maneuvered to aim the exit end 46 generally at a predetermined target area 22 having decay tissue, plaque or lesion 12 thereon. Proper aiming is indicated by the guide beam 102 impinging upon the target area 22.

After properly positioning the guide beam 102, the coolant delivery system 20 is operated so as to spray a layer of water 52 on the surface of the tooth 10. The suction system 24 is then operated so as to collect excess water 52. Next, the laser 16 is activated to produce ultraviolet radiation 18. Since the output beam 30 is substantially coincident with the guide beam 102 it impinges upon the target area 22. Finally, the light guide 44 is maneuvered as desired to cause the output beam 30 to impinge upon selected portions of the target area 22.

In accordance with the invention, the output beam 30 passes through the layer of water 52 to eradicate a desired material 12 located beneath the water 52. The water 52 is collected by the suction system 24 during ablation when necessary or continuously to prevent buildup of debris 64 and water 52.

The water 52 may be sprayed continuously so as to pool or form a thick layer on the tooth 10 during laser treatment because of the relatively weak absorption of radiation 18 by water 52 in the ultraviolet spectral region. It should be noted that the water 52 is much more effective in removing excess heat if it is sprayed on the tooth 10 simultaneously during laser irradiation. Preferably, the laser pulse duration, energy level and frequency are set prior to the ablation process. However, these parameters may be adjusted during the procedure if desired. For instance, a quicker rate of ablation may be achieved by increasing the laser energy level. The optimal fluence level for removing carious tissue 12 without causing thermal damage to surrounding areas has been found to be approximately 0.07 to 10 J/cm$^2$. Furthermore, the optimal wavelength and frequency are in the range of 193 nm–400 nm and 1–20 Hz respectively.

In the examples to follow an ArF laser was used with water as a coolant from a distilled water reservoir. Continuous water flow was used over the surface of the treated area, in this case, extracted teeth.

EXAMPLE 1

An ArF laser at fluence as low as approximately 90 mJ/cm$^2$ was caused to impinge upon carious tissue on the surface of a dry extracted tooth. Charred tissue was quickly produced and the ablation rate was found to decrease drastically thereafter. Additional experiments were performed by using a $N_2$ purge flow as coolant. Although there were some improvements gained by use of $N_2$ at a relatively high flow rate, $N_2$ did not prevent charring of the tissue effectively.

EXAMPLE 2

Example 1 was repeated except that distilled water was used as coolant. The water was flowed from the tip of a tube connected to a distilled water reservoir. Pooled water was formed on the tooth surface by continuous flow of the water. An unfocused excimer laser beam (ArF laser at 193 nm) was apertured to approximately a 1 mm-diameter beam size and was caused to penetrate through the pooled water onto the decayed tissue. The laser repetition rate was varied from 10 to 20 Hz. Under these conditions, no charred tissue was observed for a fluence up to approximately 230 mJ/cm$^2$ for a duration of up to approximately 6 minutes. The ablation (recession) rate was measured to be approximately 0.35 micrometers per pulse at a laser fluence of 200 mJ/cm$^2$, operating at 20 Hz. The recession was approximately 2.6 mm for a duration of up to approximately 6 minutes.

EXAMPLE 3

Thermocouples were used to measure the surface temperature of the surrounding area and the pulp chamber during laser irradiation. In the absence of water cooling, the temperature in the surrounding area increased by 9° C. in 3 minutes at laser fluence of 200 mJ/cm$^2$ and laser repetition rate of 20 Hz. In the presence of water flow under similar laser irradiation conditions, the temperature rise was less than 1° C. near the irradiation area and essentially no measurable temperature rise at the pulp chamber.

One advantage of the current invention is that water spray may be used without critically controlling the thickness of the layer of water as required in infrared laser procedures since ultraviolet radiation is not absorbed strongly by water. Furthermore, a continuous flow of water can be utilized thereby alleviating the need to dry the target area between pulses of radiation. Another advantage is that a thick layer of water is highly effective in preventing thermal damage at the target site, surrounding areas and in the pulp chamber since excess heat is prevented from being generated. Charring is also alleviated with water cooling and allows the uninterrupted use of higher laser power which increases the penetration depth per pulse and ablation rate. In addition, an ultraviolet laser is highly effective in selectively ablating carious material while leaving healthy dentine and enamel tissue unaffected.

Those skilled the art can now appreciate from the foregoing description that the broad teachings of the present invention can be implemented in a variety of forms. Therefore, while this invention has been described in connection with particular examples thereof, the true scope of the invention should not be so limited since other modifications will become apparent to those skilled practitioners upon a study of the drawings, specification and following claims.

What is claimed is:

1. An apparatus for removing pre-selected dental caries from non-selected healthy dental tissue at a predetermined target site of a tooth comprising:

a laser source for generating an ultraviolet laser beam having a wavelength in a range of 193 nm–400 nm;

a fluid coolant delivery handpiece coupled to a water reservoir for delivering a fluid coolant for dissipating heat to said target site such that said fluid coolant has an arbitrary thickness between said laser beam and said preselected dental caries and said non-selected healthy dental tissue; and an optical device disposed in radiation receiving relation to said laser source for delivering said laser beam to said target site, said laser beam propagating through said fluid coolant and ablating said pre-selected dental caries, said fluid coolant coacting with said laser beam to maintain a temperature at said target site below a given threshold temperature as said pre-selected dental caries are removed by said laser beam.

2. The apparatus of claim 1 further comprising a low power laser generator for generating a laser guide beam having a wavelength in the visible spectrum, said laser guide beam being directed so as to coincide with said laser beam at said target site for providing a visible reference for directing said laser beam.

3. The apparatus of claim 1 further comprising a vacuum means for removing said fluid coolant and pre-selected dental caries from said target site.

4. The apparatus of claim 1 wherein said optical device includes a radiation emitting end for focusing said laser beam to a desired diameter at said target site.

5. The apparatus of claim 1 wherein said optical device further comprises a fiber optic wave guide having a first end and a second end, said first end optically communicating with said laser source for receiving said laser beam therein, and said second end being positionable to said target site and operable for focusing said laser beam to a desired diameter at said target site.

6. The apparatus of claim 1 wherein said wavelength of said laser beam is in a range of 240 nm–400 nm.

7. The apparatus of claim 1 wherein said laser beam comprises an Nd:YAG laser beam having a wavelength in a range of 260–360 nm.

8. The apparatus of claim 1 wherein said laser beam has a fluence level in a range of 0.01–10 J/cm$^2$ at said target site.

9. The apparatus of claim 1 wherein said laser beam has a frequency level in a range of 1–1000 Hz.

10. The apparatus of claim 1 wherein said laser beam has a diameter at said target site in a range of 0.1 mm–5 mm.

11. The apparatus of claim 1 wherein said fluid coolant comprises water.

12. A method of removing pre-selected dental caries from non-selected healthy dental tissue at a target site of a tooth comprising:

delivering a fluid coolant for dissipating heat to said target site such that said fluid coolant forms a layer having an arbitrary thickness on said preselected dental caries and said non-selected healthy dental tissue;

generating a laser beam having a wavelength in a range of 193 nm–400 nm; and delivering said laser beam to said target site, said laser beam propagating through said fluid coolant and ablating said pre-selected dental caries, said fluid coolant coacting with said laser beam to maintain a temperature at said target site below a given threshold temperature.

13. The method of claim 12 further comprising:

generating a low power laser guide beam having a wavelength in the visible spectrum and directing said low power laser guide beam so as to be coincident with said laser beam at said target site.

14. The method of claim 12 further comprising:

removing said fluid coolant and aid pre-selected dental caries from said target site with a vacuum after said laser beam ablates said pre-selected material.

15. The method of claim 12 further comprising:

focusing said laser beam to a given diameter at said target site.

16. The method of claim 12 wherein said step of generating said laser beam includes generating an Nd:YAG laser beam having a wavelength in a range of 260 nm–360 nm.

17. A method of ablating pre-selected dental caries from a non-selected healthy dental tissue at a target site of a tooth comprising:

delivering water for dissipating heat to said target site such that said water forms a layer having an arbitrary thickness on said preselected caries an non-selected tissue;

generating a laser beam having a wavelength in a range of 193 nm–400 nm, a fluence level in a range of 0.01–10 $J/cm^2$ and a frequency level in a range of 1–1000 Hz;

generating a low power laser guide beam having a wavelength in the visible spectrum, said low power laser guide beam being coincident with said laser beam at said target site;

delivering said low power guide beam and said laser beam to said target site through a fiber optic waveguide, said waveguide focusing said laser beam to a diameter in a range of 0.1 nm–5 nm at said target site, said laser beam propagating through said water and ablating said pre-selected caries from said non-selected healthy dental tissue at said target site, said water coacting with said laser beam to maintain a temperature at said target site below a given threshold temperature; and removing said water and pre-selected caries from said target site with a vacuum after said laser beam ablates said pre-selected caries.

18. The method of claim 17 wherein said step of generating said laser beam includes generating an Nd:YAG laser beam at a wavelength in a range of 260–360 nm.

\* \* \* \* \*